(12) United States Patent
Abe et al.

(10) Patent No.: US 7,944,466 B2
(45) Date of Patent: May 17, 2011

(54) ENDOSCOPE APPARATUS

(75) Inventors: Kazunori Abe, Saitama (JP); Shinji Takeuchi, Saitama (JP); Daisuke Ayame, Saitama (JP)

(73) Assignee: Fujinon Corporation, Saitama (JP)

( * ) Notice: Subject to any disclaimer, the term of this patent is extended or adjusted under 35 U.S.C. 154(b) by 1476 days.

(21) Appl. No.: 11/365,947

(22) Filed: Mar. 2, 2006

(65) Prior Publication Data

US 2006/0198551 A1  Sep. 7, 2006

(30) Foreign Application Priority Data

Mar. 4, 2005  (JP) ................ P.2005-060197

(51) Int. Cl.
*H04N 9/47* (2006.01)
*H04N 5/228* (2006.01)
*H04N 5/202* (2006.01)
*H04N 5/217* (2011.01)
*G06K 9/00* (2006.01)
*G06K 9/40* (2006.01)
*A61B 1/00* (2006.01)
*A61B 1/04* (2006.01)

(52) U.S. Cl. ......... 348/71; 348/65; 348/222.1; 348/254; 348/241; 382/128; 382/165; 382/274; 600/101; 600/109

(58) Field of Classification Search ............. 348/65–76, 348/222.1, 254, 241; 382/128, 131, 132, 382/165, 167, 260, 274, 275; 600/101–183

See application file for complete search history.

(56) References Cited

U.S. PATENT DOCUMENTS

| | | | | |
|---|---|---|---|---|
| 4,884,133 | A | * | 11/1989 | Kanno et al. ................ 358/98 |
| 4,885,634 | A | | 12/1989 | Yabe |
| 5,092,331 | A | * | 3/1992 | Nakamura et al. .......... 600/342 |
| 5,408,263 | A | * | 4/1995 | Kikuchi et al. ............... 348/68 |
| 5,675,378 | A | | 10/1997 | Takasugi et al. |
| 5,868,666 | A | * | 2/1999 | Okada et al. ................ 600/118 |
| 7,204,803 | B2 | * | 4/2007 | Ueno et al. ................. 600/109 |
| 2004/0215060 | A1 | * | 10/2004 | Ueno et al. ................. 600/160 |
| 2006/0211915 | A1 | * | 9/2006 | Takeuchi et al. ............ 600/109 |
| 2009/0289200 | A1 | * | 11/2009 | Ishii ......................... 250/459.1 |

FOREIGN PATENT DOCUMENTS

| | | |
|---|---|---|
| EP | 1 302 152 A1 | 4/2003 |
| EP | 1 491 132 A1 | 12/2004 |
| JP | 1-113022 | 5/1989 |

(Continued)

OTHER PUBLICATIONS

Japanese Notification of Reason for Refusal, May 26, 2010.

*Primary Examiner* — Lin Ye
*Assistant Examiner* — Marly Camargo
(74) *Attorney, Agent, or Firm* — Birch, Stewart, Kolasch & Birch, LLP

(57) ABSTRACT

An endoscope apparatus comprises: an endoscope comprising an imaging device that forms a color image signal of a body to be observed; a storage portion that stores matrix data for forming a spectral image based on the color image signal; a spectral image-forming circuit that conducts matrix calculation based on the color image signal by using the matrix data of the storage portion and forms at least one spectral image signal each of which corresponds to an arbitrarily selected wavelength range; and an amplifier circuit that amplifies said at least one spectral image signal formed by the spectral image-forming circuit.

4 Claims, 4 Drawing Sheets

FOREIGN PATENT DOCUMENTS

| | | |
|---|---|---|
| JP | 02-107070 | 4/1990 |
| JP | 2-299633 | 12/1990 |
| JP | 11-225954 | 8/1999 |
| JP | 2002-369797 | 12/2002 |
| JP | 2003-93336 A | 4/2003 |
| JP | 2003093336 A * | 4/2003 |

* cited by examiner

ENDOSCOPE APPARATUS

BACKGROUND OF THE INVENTION

1. Field of the Invention

The present invention relates to an endoscope apparatus, more particularly, a constitution used in medical fields for forming and displaying a spectral image (video) made up of image information of arbitrarily selected wavelength ranges.

2. Description of the Related Art

Recently, in an electronic endoscope apparatus which uses a solid imaging device, spectral imaging combined with a narrow band pass filter on the basis of a spectral reflectance in the alimentary canal (gastric mucosa and the like), namely, a narrow band filter built-in an electronic endoscope apparatus (Narrow Band Imaging-NBI) has become the focus of attention. In place of rotational filters of R (red), G (green) and B (blue) by a frame sequential method, this system is provided with band pass filters of three narrow bands (wavelengths), outputs sequentially illumination light via these narrow bandpass filters, and conducts processing the same as in the case of red (R), green (G) and blue (B) signals while changing respective weightings to three signals obtained from these illumination lights, thereby forming a spectral image. This spectral image is able to realize microstructures and the like in gastrointestinal tracts such as the stomach and large intestine, which would otherwise not be realized.

In contrast, unlike the frame sequential method using the above-described narrow band pass filters, as described in Japanese Published Unexamined Patent Application No. 2003-93336, it has been proposed that in the simultaneous method in which micro-mosaic color filters are arranged on a solid imaging device, a spectral image is formed by the computing process on the basis of image signals obtained from white light. In this method, the relationship between numeric data of the respective R, G, and B color sensitivity characteristics and numeric data of spectral characteristics of a specific narrow bandpass is determined as matrix data (coefficient sets) and computing is made for the matrix data and the R, G and B signals to obtain spectral image signals artificially via the narrow bandpass filters. Where a spectral image is formed by such computing, it is not necessary to provide a plurality of filters corresponding to desired wavelength ranges and to provide these change-over arrangements, there by successfully avoiding increases in the size of a system and reducing cost.

However, since each wave range of the signals constituting a spectral image is a narrow band on formation of the spectral image in the endoscope apparatus, the image is reduced in brightness as compared with an ordinary image formed by RGB signals, which is a problem. FIG. 5 shows spectral sensitivity characteristics of color filters such as R (red), G (green) and B (blue) used in an elementary color-type CCD, a solid imaging device, and an example of individual wavelength ranges forming the spectral image in the present invention. As shown in this drawing, the spectral image is constituted with signals made up of, for example, wave range $\lambda 1$ (narrow band centered at 500 nm), wave range $\lambda 2$ (narrow band centered at 620 nm) and wave range $\lambda 3$ (narrow band centered at 650 nm) These wavelength ranges of $\lambda 1$, $\lambda 2$ and $\lambda 3$ are reduced, as compared with a RGB wave range, and they are a narrow band. Therefore, all signal components in the wavelength ranges of $\lambda 1$, $\lambda 2$ and $\lambda 3$ are extremely reduced, as compared with all signal components in the RGB wave range, and lacking in brightness components.

Further, in formation of an ordinary image, output signals of a CCD are amplified to result in an increase in noise components, and therefore the noise components of the image signal are also removed. In formation of a spectral image as well, care must be taken so as not to increase noise components when signals of individual wavelength ranges are amplified.

In addition, in a spectral image which has become the focus of attention, microstructures and others can be visualized, which has not conventionally been obtained. If specified microstructures are displayed so as to be remarkably distinguished from other tissues, valuable information on an object to be observed can be provided useful for making a diagnosis and others.

SUMMARY OF THE INVENTION

The present invention has been made in view of the problem, an object of the present invention is to provide an endoscope apparatus capable of preventing a reduction in brightness due to wavelength ranges of a narrow band, suppressing an increase in noise components and also providing valuable information on an object to be observed in which specified microstructures are extracted.

In order to attain the above-described object, an endoscope apparatus according to the first aspect of the invention comprises: an endoscope comprising an imaging device (at its distal end) that forms a color image signal of a body to be observed; a storage portion that stores matrix data (coefficient data) for forming a spectral image based on the color image signal; a spectral image-forming circuit that conducts matrix calculation based on the color image signal by using the matrix data of the storage portion and forms at least one spectral image signal each of which corresponds to an arbitrarily selected wavelength range; and an amplifier circuit that amplifies said at least one spectral image signal formed by the spectral image-forming circuit.

According to the second aspect of the invention, there is provided the endoscope apparatus, wherein said at least one spectral image signal comprises a plurality of spectral image signals corresponding to a plurality of wavelength ranges, and the amplifier circuit amplifies said plurality of image signals at individual different gains (individual different amplification rates).

According to the third aspect of the invention, there is provided the endoscope apparatus, wherein the color image signal from the imaging device is selectably: (i) passed through the spectral image-forming circuit to form said at least one spectral image signal; or (ii) not passed through the spectral image-forming circuit to form an ordinary color image signal for an ordinary display, and wherein the endoscope apparatus further comprises a noise removal circuit for removing noise of the ordinary color image signal or said at least one spectral image signal, and the noise removal circuit conducts noise processing for said at least one spectral image signal at a first noise removal rate and conducts noise processing for the ordinary color image signal at a second noise removal rate, the first noise removal rate being higher than the second noise removal rate.

According to the fourth aspect of the invention, there is provided the endoscope apparatus, wherein the noise removal circuit increases the first noise removal rate as a gain of the amplifier circuit increases, and the noise removal circuit decreases the first noise removal rate as a gain of the amplifier circuit decreases.

According to the fifth aspect of the invention, there is provided the endoscope apparatus, wherein the color image signal input to the spectral image-forming circuit is: (i) obtained by releasing gamma correction in a signal processing circuit at a front stage of the spectral image-forming circuit; or (ii) obtained via a reverse gamma-correction processing circuit, and wherein the spectral image-forming circuit forms said at least one spectral image signal based on the color image signal to which no gamma correction is given, and then gamma correction is provided to said at least one spectral image signal.

In the above-described constitution, matrix data (coefficient sets) for determining $\lambda 1$, $\lambda 2$ and $\lambda 3$ signals which are a narrow-band wavelength (component) from RGB signals are stored in the operation memory of a processor unit. When an operator selects three wavelength ranges (one wave range may be selected) for forming a spectral image, matrix data corresponding to the three wavelength ranges are read from the memory, and $\lambda 1$, $\lambda 2$ and $\lambda 3$ signals are formed from RGB signals output from the matrix data, a DSP and others. Thereafter, these $\lambda 1$, $\lambda 2$ and $\lambda 3$ signals are amplified by an amplifier circuit to a predetermined gain, thereby increasing brightness up to the level as with formation of an ordinary image. Therefore, a spectral image in combination with selected three wavelength ranges is displayed on a monitor in a desired brightness.

With the constitution according to the second aspect, wavelength ranges of $\lambda 1$, $\lambda 2$ and $\lambda 3$ capable of extracting specific microstructures, for example, blood vessels, are selected, and, of these ranges, the gain of $\lambda 3$ signal (for example, red color zone) is amplified 1.2 times that of $\lambda 1$ or $\lambda 2$ signal, thereby making it possible to form and display an image at which specific blood vessel structures are highlighted. Further, as described above, where $\lambda 1$, $\lambda 2$ and $\lambda 3$ signals are amplified, noise components are also amplified, resulting in deterioration in image quality. Therefore, in the constitution according to the third aspect, a noise removal circuit is provided to conduct noise processing at a higher noise removal rate than that of the noise processing for forming color image signals for an ordinary display. For example, the number of frame images for comparing noise processing (equation) can be increased to elevate the noise removal rate (effect).

Further, in forming color image signals at an endoscope apparatus, gamma correction is conducted so that image signals to be input to an indicator are proportionally related to the image brightness at the indicator. In the gamma correction, underlying image signals are deformed and therefore not appropriate as an image signal for forming the spectral image. Then, in the constitution according to the fifth aspect, gamma-correction processing of the DSP and others in the previous stage is released or a reverse gamma-correction processing circuit is provided to return gamma correction to an original state, thereby forming a spectral image on the basis of color image signals to which no gamma correction is given.

DETAILED DESCRIPTION OF THE INVENTION

Figure 1:
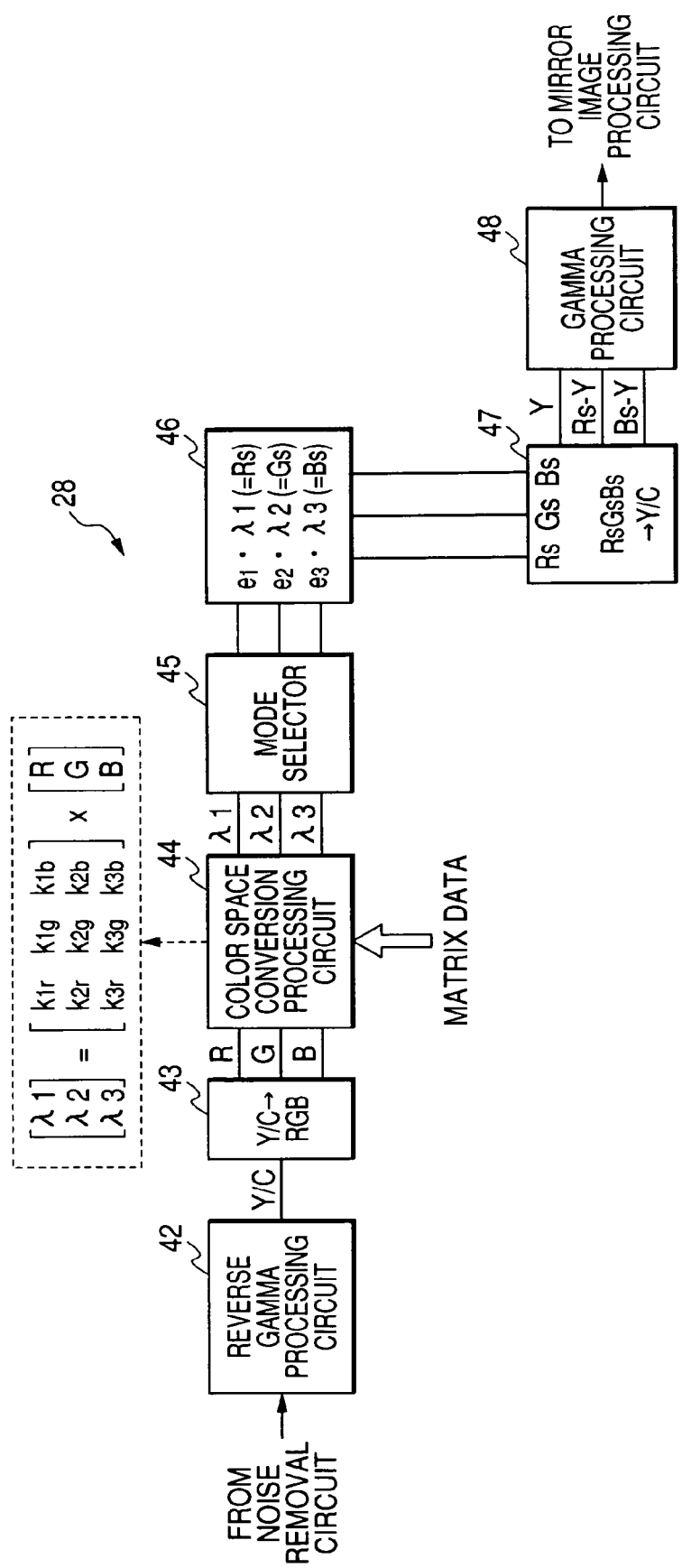
FIG. 1 is a block diagram showing the constitution of the spectral image-forming circuit of the endoscope apparatus according to an embodiment of the present invention.
Figure 2:
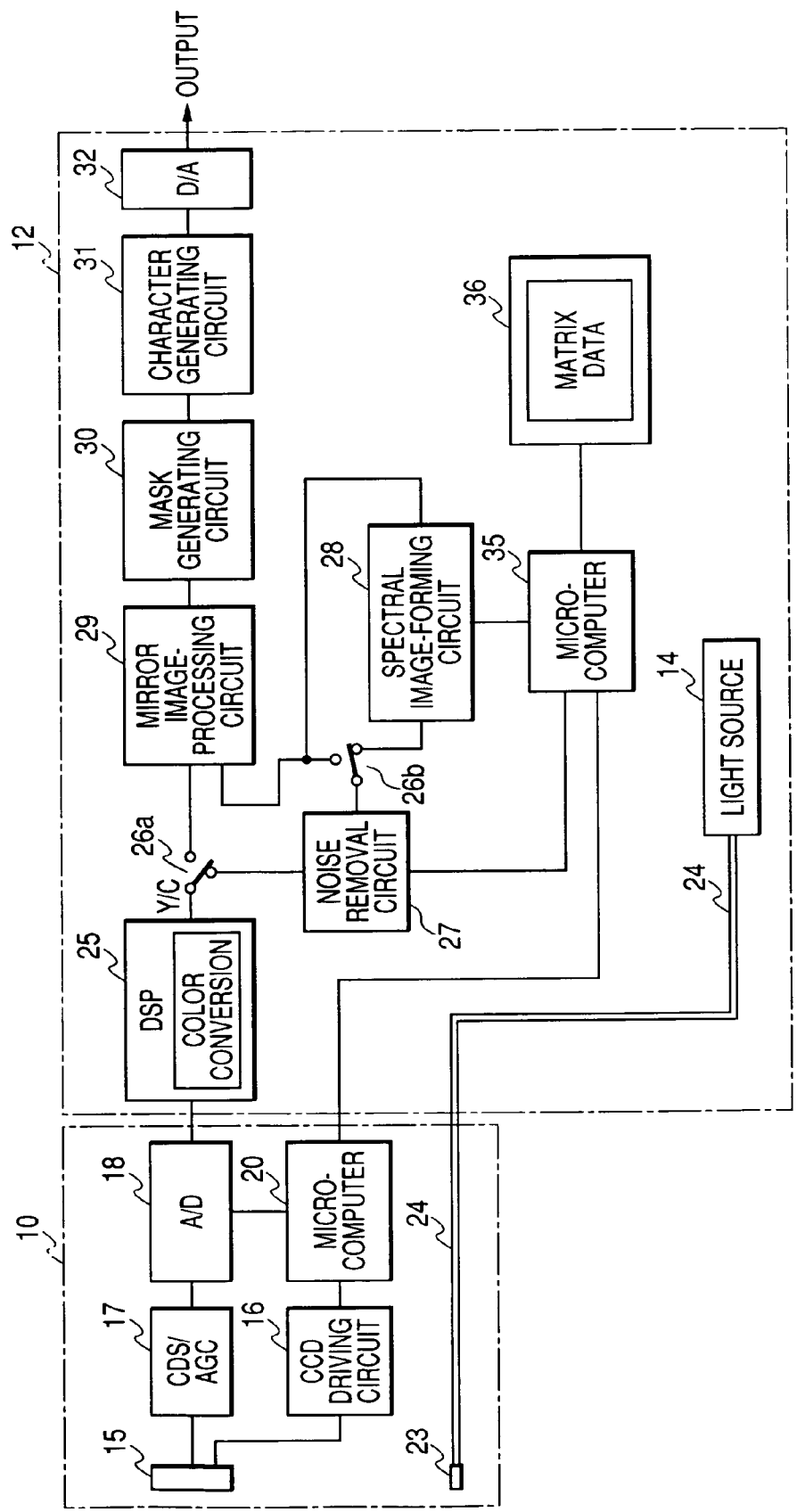
FIG. 2 is a block diagram showing the constitution of the endoscope apparatus according to the embodiment.

FIG. 1 and FIG. 2 show a constitution of the electronic endoscope apparatus according to an embodiment in the present invention. As shown in FIG. 2, the electronic endoscope apparatus is constituted in such a manner that a scope (electronic endoscope) 10 is connected to a processor unit 12 in a freely attachable and detachable way and a light source 14 is arranged in the processor unit 12. Further, there is a case where the light source 14 may be arranged on a light source unit, which is a separate body. The scope 10 is provided on the end with a CCD 15 which is a solid imaging device, and the CCD 15 includes, for example, a complementary color-type CCD having color filters of Mg (magenta), Ye (yellow), Cy (cyan) and G (green) and an elementary color-type CCD having R, G and B color filters on an imaging surface.

The CCD 15 is provided with a CCD driving circuit 16 for forming a driving pulse on the basis of synchronizing signals, a CDS/AGC (correlated dual sampling/automatic gain control) circuit 17 for sampling and amplifying an image (video) signal input from the CCD 15 the image signal and an A/D converter 18. Also arranged is a microcomputer 20 of or controlling various circuits inside the scope 10 and also controlling communications with the processor unit 12. Further, the scope 10 is provided at the end with an illumination window 23, which is connected to the light source 14 by a light guide 24.

The processor unit 12 is provided with a DSP (digital signal processor) 25 which imparts a variety of image processings to digitally converted image signals. In the DSP 25, Y/C signals constituted by a brightness (Y) signal and a color difference [C(R−Y, B−Y)] signal are formed and output from the output signal of the above-described CCD 15. In the embodiment, ordinary images (moving image and still image) and spectral images (moving image and still image) can be selectively formed and displayed, and the DSP 25 is provided with a noise removal (noise reduction) circuit 27 for removing noise of the image signal input from the DSP 25 via a selector 26a. Further, a spectral image-forming circuit 28 is connected via the selector 26b for selectively forming an ordinary image or a spectral image (to one terminal). Arranged on the other terminal of the selector 26b are a mirror image-processing circuit 29 for inverting a mirror image, a mask generating circuit 30 for generating a mask covering the periphery of the image on the indicator screen, a character generating circuit 31 for generating characters indicating operating conditions, information on patients and others, and a D/A converter 32.

Also provided is a microcomputer 35 which controls the respective circuits inside the processor unit 12 and reads matrix (coefficient) data from a memory 36 (corresponding to the storage portion) to impart the data to the spectral image-forming circuit 28. Matrix data (table) for forming a spectral image on the basis of RGB signals are stored in the memory 36.

FIG. 1 shows details inside the spectral image-forming circuit 28. The spectral image-forming circuit 28 is provided with a reverse gamma processing circuit for conducting reverse gamma ($\gamma$) correction (FIG. 4), a first color conversion circuit 43 for converting brightness (Y)/color difference (C)

signals to RGB signals and a color-space conversion processing circuit 44 for conducting matrix calculation for a spectral image in relation to the RGB signals. The color-space conversion processing circuit 44 outputs selected spectral image signals of λ1, λ2 and λ3 wavelength ranges.

Table 1 shows the matrix data used for conducting matrix calculation in the color-space conversion processing circuit 44 and accommodated in the memory 36.

TABLE 1

| Parameter | $k_{pr}$ | $k_{pg}$ | $k_{pb}$ |
|---|---|---|---|
| p1 | 0.000083 | −0.00188 | 0.003592 |
| . | . | . | . |
| . | . | . | . |
| . | . | . | . |
| p18 | −0.00115 | 0.000569 | 0.003325 |
| p19 | −0.00118 | 0.001149 | 0.002771 |
| p20 | −0.00118 | 0.001731 | 0.0022 |
| p21 | −0.00119 | 0.002346 | 0.0016 |
| p22 | −0.00119 | 0.00298 | 0.000983 |
| p23 | −0.00119 | 0.003633 | 0.000352 |
| . | . | . | . |
| . | . | . | . |
| . | . | . | . |
| p43 | 0.003236 | 0.001377 | −0.00159 |
| p44 | 0.003656 | 0.000671 | −0.00126 |
| p45 | 0.004022 | 0.000068 | −0.00097 |
| p46 | 0.004342 | −0.00046 | −0.00073 |
| p47 | 0.00459 | −0.00088 | −0.00051 |
| p48 | 0.004779 | −0.00121 | −0.00034 |
| p49 | 0.004922 | −0.00148 | −0.00018 |
| p50 | 0.005048 | −0.00172 | −3.6E−05 |
| p51 | 0.005152 | −0.00192 | 0.000088 |
| p52 | 0.005215 | −0.00207 | 0.000217 |
| . | . | . | . |
| . | . | . | . |
| . | . | . | . |
| p61 | 0.00548 | −0.00229 | 0.00453 |

The matrix data shown in the above Table 1 includes, for example, 61 wavelength-range parameters (coefficient sets) p1 to P61 in which a wavelength range of 400 nm to 700 nm is divided at 5 nm intervals. The parameters p1 to p61 are constituted by coefficients, $k_{pr}$, $k_{pg}$ and $k_{pb}$ (p corresponds to p1 to p61) for matrix calculation.

Then, in the color space conversion processing circuit 44, matrix calculation is carried out according to the following mathematical formula 1 by referring to the above coefficients, $k_{pr}$, $k_{pg}$ and $k_{pb}$, and RGB signals output from the first color conversion circuit 43.

$$\begin{bmatrix} \lambda 1 \\ \lambda 2 \\ \lambda 3 \end{bmatrix} = \begin{bmatrix} k_{1r} & k_{1g} & k_{1b} \\ k_{2r} & k_{2g} & k_{1b} \\ k_{3r} & k_{3g} & k_{3b} \end{bmatrix} \times \begin{bmatrix} R \\ G \\ B \end{bmatrix}$$ [Mathematical Formula 1]

More specifically, where the parameters, for example, p21 (center wavelength 500 nm), p45 (center wavelength 620 nm) and p51 (center wavelength 650 nm) shown in Table 1, are selected as λ1, λ2 and λ3, (−0.00119, 0.002346 and 0.0016) of p21, (0.004022, 0.000068 and −0.00097) of p45 and (0.005152, −0.00192 and 0.000088) of p51 may be substituted as coefficients ($k_{pr}$, $k_{pg}$ and $k_{pb}$).

Then, the color-space conversion processing circuit 44 is provided with a mode selector 45 for selecting either a spectral image of one waverange (narrowband) (monochrome mode) or a spectral image of three wavelength ranges (three-color mode) (the mode selector may be provided with a two-color mode for selecting two colors). The mode selector 45 is connected at the rear stage with an amplifier circuit 46 (automatic gain control circuit and the like may be acceptable). The amplifier circuit 46 gives the gain values $e_1$, $e_2$ and $e_3$, to λ1, λ2 and λ3 signals for forming a spectral image, respectively, there by outputting amplified signals of $e_1 \times \lambda 1$, $e_2 \times \lambda 2$ and $e_3 \times \lambda 3$. Further, where a monochrome mode is selected, any one of the λ1, λ2 and λ3 signals is amplified.

The amplifier circuit 46 is provided with a second color conversion circuit 47 for inputting λ1, λ2 and λ3 signals amplified by gain values of $e_1$, $e_2$ and $e_3$, as Rs, Gs and Bs signals, in order to conduct a processing which corresponds to conventional RGB signals and converting Rs, Gs and Bs signals to Y/C signals and a gamma processing circuit 48 for conducting 48 γ correction. Output signals of the gamma processing circuit 48 are supplied to the mirror image processing circuit 29 shown in FIG. 2.

Figure 3:
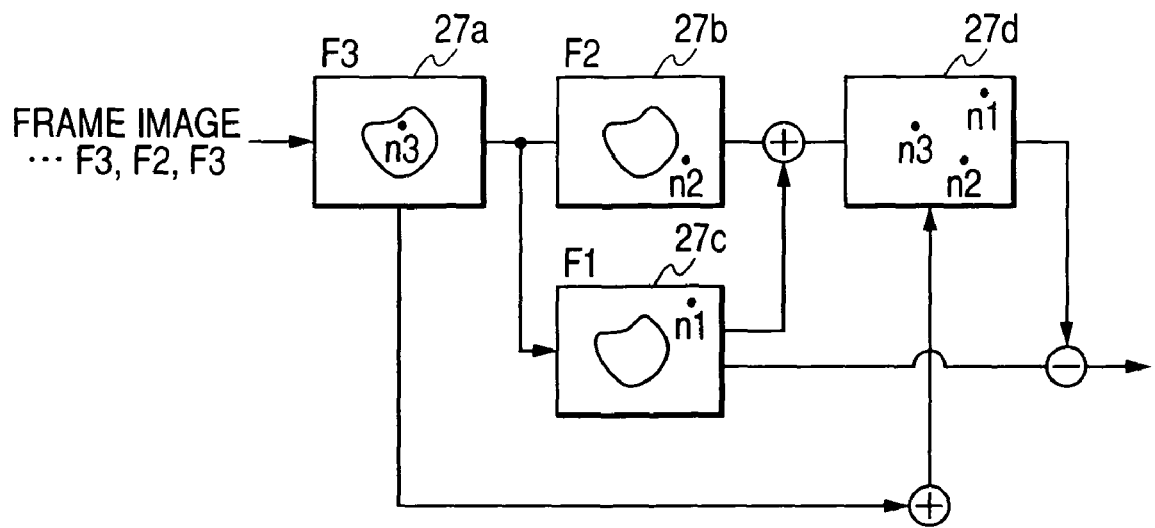
FIG. 3 is a diagram showing the operation and the constitution inside the noise removal circuit.

FIG. 3 shows a movement constitution example of the above-described noise removal circuit 27. Frame images such as F1, F2, F3 . . . are input sequentially to the noise removal circuit 27. An image F1 of the memory portion 27*c* and an image F2 of the memory portion 27*b* are added at a coefficient ratio of 1/(final comparison number), for example, and sent to a comparison portion 27*d*. An image F3 of the memory portion 27*a* is also added to images of F1+F2 at the coefficient ratio and compared at the comparison portion 27*d*. Consequently, as shown at the comparison portion 27*d*, signals of noise n1, n2 and n3 for the respective images can be obtained and these signals of noise n1, n2 and n3 are deducted from an image signal of F1, thereby removing noise n1 of the image F1. More specifically, noise components in principle do not exist at the same place on the screen. If a plurality of images (F1, F2, F3 . . . ) are added for comparison (or equation), the noise components become small and in removing noise the number of frame images to be processed such as comparison can be increased to elevate the noise removal rate. In the noise removal circuit 27 of the present embodiment, where one (or two) images are compared in forming an ordinary image, two or more (three or more) images are to be compared in forming a spectral image.

Further, in the noise removing processing, when gain values $e_1$, $e_2$ and $e_3$ are elevated in the amplifier circuit 46, the noise removal rate is also elevated accordingly. More specifically, depending on elevation (lowering) of the gain values $e_e$, $e_2$ and $e_3$ images to be compared are increased from two to three or from three to four (or decreased). Further, another noise removing processing can also be used in addition to the foregoing. The DSP 25 may be arranged on the scope 10.

The embodiment is constituted as described above. As shown in FIG. 2, in the scope 10, the CCD driving circuit 16 drives the CCD 15, by which imaging signals of an object to be observed are output from the CCD 15. The signals are subjected to the correlated dual sampling at the CDS/AGC circuit 17 and to the amplification by the automatic gain control, and then supplied via the A/D converter 18 to the DSP 25 of the processor unit 12 as a digital signal. In the DSP 25, gamma processing is given to output signals from the scope 10, and also color conversion processing is given to signals obtained via color filters of Mg, Ye, Cy and G, thereby forming Y/C signals made up of a brightness (Y) signal and a color difference (R−Y, B−Y) signal. Output of the DSP 25 is usually supplied, as an ordinary color image signal, to a mirror image processing circuit 29, a mask generating circuit 30 and a character generating circuit 31 by the selector 26*a* (also by the selector 26*b* when the noise removal circuit 27 is used). After a predetermined processing at these circuits, the output is supplied via the D/A converter 32 to a monitor, and ordinary color images of an object to be observed are displayed on the monitor.

When an operating switch arranged on an operation portion and others for forming a spectral image are depressed, the selectors 26a and 26b changes Y/C signals output from the DSP 25 so as to be supplied to the spectral image-forming circuit 28 via the noise removal circuit 27. In the noise removal circuit 27, noise components are removed from the Y/C signals. As described with reference to FIG. 3, where a two-frame image (obtained according to time sequence) as an image to be compared in forming an ordinary color image, an image made up of three frames or more is compared to conduct processing at a higher noise removal rate.

Figure 4:
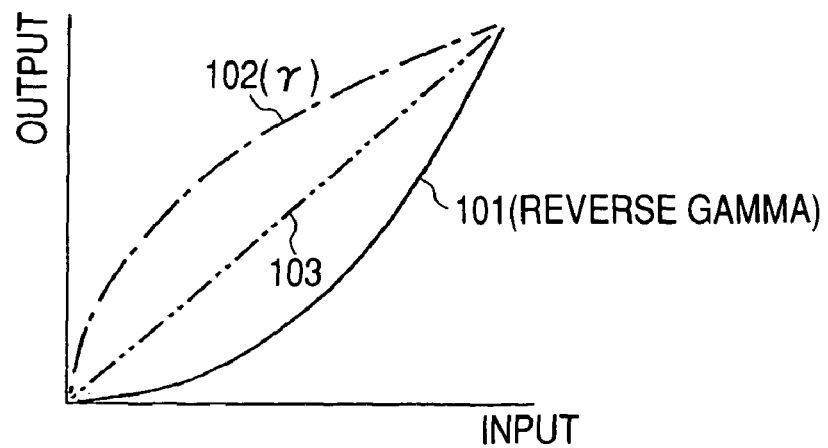
FIG. 4 is a graph chart showing characteristics of the reverse gamma correction and the gamma correction according to the embodiment.

In this instance, since three wavelength ranges of $\lambda 1$, $\lambda 2$ and $\lambda 3$ signals are selected by an operator, the microcomputer 35 reads matrix (coefficient) data corresponding to the three selected wavelength ranges from the memory 36 (Table 1) to supply the data to the spectral image-forming circuit 28. Then, in the spectral image-forming circuit 28 shown in FIG. 1, a reverse gamma ($\gamma$) processing circuit 42 conducts a reverse gamma correction. More specifically, as shown in FIG. 4, the relationship between the input signal and the output signal can be given as a curve (quadratic curve) 101 in view of the characteristics of a CRT indicator and others. In the DSP 25, gamma correction which is a curve 102 is provided so that the relationship between the input and the output can be given as linear characteristics 103. Then, in the reverse gamma processing circuit 42, the curve 101 is subjected to the reverse gamma correction, by which the signals are restored to an original state before gamma correction. It is, therefore, possible to avoid the distortion of matrix calculation for forming a spectral image in a subsequent stage.

The out put of the reverse gamma processing circuit 42 is supplied to a color-space conversion processing circuit 44 after conversion of Y/C signals to RGB signals by a first color conversion circuit 43. In the color-space conversion processing circuit 44, matrix calculation is conducted according to the mathematical formula 1 for forming a spectral image by referring to the RGB signals and matrix data. For example, where p21 (center wavelength 500 nm), p45 (center wavelength 620 nm) and p51 (center wavelength 650 nm) are selected as three wavelength ranges ($\lambda 1$, $\lambda 2$ and $\lambda 3$), signals of $\lambda 1$, $\lambda 2$ and $\lambda 3$ can be determined from the RGB signals by matrix calculation according to the following mathematical formula 2.

[Mathematical formula 2]

$$\begin{bmatrix} \lambda 1 \\ \lambda 2 \\ \lambda 3 \end{bmatrix} = \begin{bmatrix} -0.00119 & 0.002346 & 0.0016 \\ 0.004022 & 0.000068 & -0.00097 \\ 0.005152 & -0.00192 & 0.000088 \end{bmatrix} \times \begin{bmatrix} R \\ G \\ B \end{bmatrix}$$

Where a three-color mode is selected by a mode selector 45, $\lambda 1$, $\lambda 2$ and $\lambda 3$ signals are supplied to an amplifier circuit 46, and where a monochrome mode is selected, any one of the $\lambda 1$, $\lambda 2$ and $\lambda 3$ signals is supplied thereto. Then, the signals are amplified by the respective gain values of $e_1$, $e_2$ and $e_3$ to obtain signals of $e_1 \times \lambda 1$, $e_2 \times \lambda 2$ and $e_3 \times \lambda 3$. These gains of $e_1$, $e_2$ and $e_3$ are given the same value in forming a basic spectral image and the $\lambda 1$, $\lambda 2$ and $\lambda 3$ signals are amplified at the corresponding rate, thereby making it possible to amplify signals without loss of the information included in the selected wavelength components.

The gains of $e_1$, $e_2$ and $e_3$ may be given a different value depending on the selected wavelength ranges as $\lambda 1$, $\lambda 2$ and $\lambda 3$ signals. In this case, the noise removal rate is increased in the noise removal circuit 27, depending on respective increased gains of the $\lambda 1$, $\lambda 2$ and $\lambda 3$ signals, and images to be compared are increased, for example, from two frames to three or four frames, thereby forming a favorable spectral image in which noise is reduced.

Amplified signals output from the amplifier circuit 46 are supplied to a second color conversion circuit 47 as signals of Rs ($=e_1 \cdot \lambda 1$), Gs ($=e_2 \cdot \lambda 2$) and Bs ($=e_3 \cdot \lambda 3$). Further, where a monochrome mode is selected, any one of the signals of $\lambda 1$, $\lambda 2$ and $\lambda 3$ (for example, $e_2 \cdot \lambda 2$ when $\lambda 2$ is selected) is supplied to the second color conversion circuit 47 as signals of Rs, Gs and Bs. In the second color conversion circuit 47, $\lambda 1$, $\lambda 2$ and $\lambda 3$ signals which are amplified as signals of Rs, Gs and Bs are converted to Y/C signals (Y, Rs–Y and Bs–Y) and thereafter supplied to a gamma ($\gamma$) processing circuit 48. As described above, a reverse gamma correction is conducted for forming a spectral image, or gamma correction is conducted so that the input and the output can be linear when the image is displayed on a monitor. Then, the output of the gamma processing circuit 48 is supplied to a mirror image processing circuit 29 shown in FIG. 2 and thereafter processed in a similar way as forming an ordinary image. A spectral image signal is supplied via a D/A converter 32 to a monitor and others.

Figure 5:
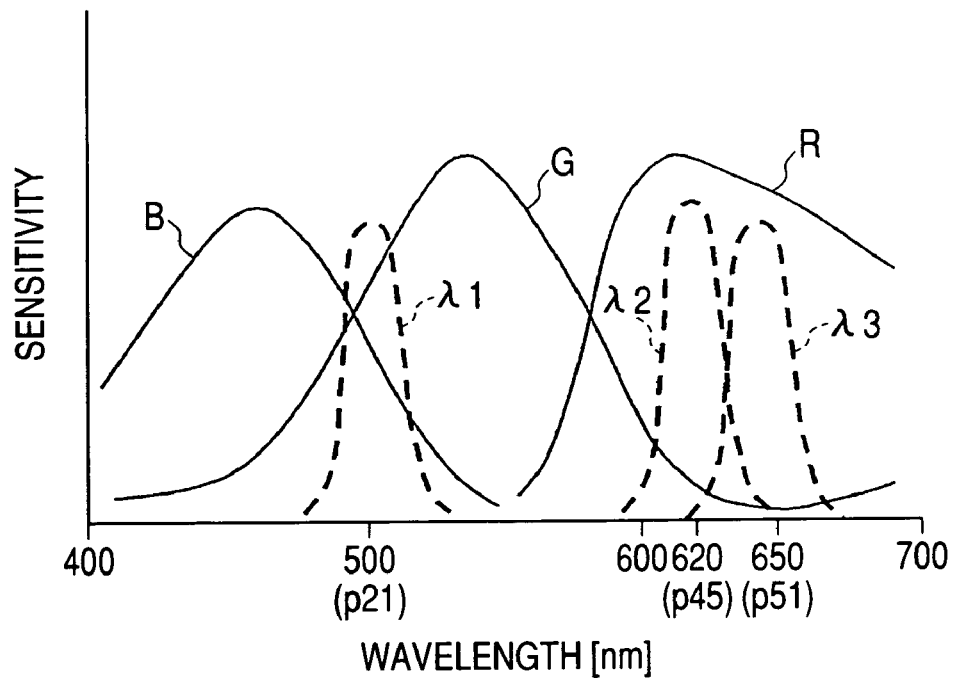
FIG. 5 is a graph chart showing an example of the wave range of a spectral image formed in the embodiment, together with spectral sensitivity characteristics of an elementary color-type CCD.
Figure 6:
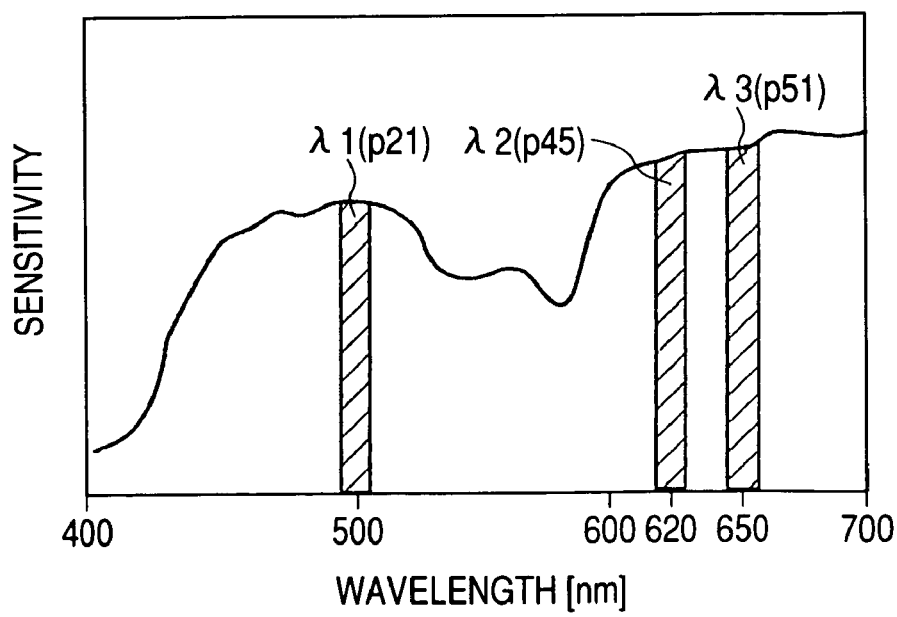
FIG. 6 is a graph chart showing an example of the wave range of a spectral image formed in the embodiment, together with the reflection spectrum of a body.

As described above, a spectral image displayed on a monitor and others is constituted by color components of wavelength ranges shown in FIG. 5 and FIG. 6. More specifically, FIG. 5 is conceptual diagram in which three wavelength ranges forming a spectral image are superimposed on spectral sensitivity characteristics of color filters on the CCD 15 (the color filter is not in agreement with the sensitivity graduation of wavelength ranges corresponding to $\lambda 1$, $\lambda 2$ and $\lambda 3$ signals). FIG. 6 is a conceptual diagram in which three wavelength ranges are superimposed on the reflection spectrum of the body. The wavelengths of p21, p45 and p51 selected as $\lambda 1$, $\lambda 2$ and $\lambda 3$ signals in the embodiment are color signals having the wave range of approximately ±10 nm, with the center wavelength being 500 nm, 620 nm and 650 nm in sequence, as illustrated in the diagram. Displayed are spectral images (moving image and still image) constituted by combinations of colors of the three wavelength ranges.

Next, a description is given for a case where a gain of the amplifier circuit 46 is set to a different value to extract specifically colored microstructures such as blood vessels and cancerous tissues. More specifically, if a wave range made up of narrow bands is selected, which constitutes a specific color showing blood vessels or cancerous tissues, a spectral image which extracts and high lights the specific color concerned can be obtained. Where a wave range capable of visualizing blood vessels is selected as $\lambda 1$, $\lambda 2$ and $\lambda 3$ signals and a red wave range is established, for example, a gain of $\lambda 3$ ($e_3$) is made 1.2 times greater than a gain of $\lambda 1$ ($e_1$) and gain of $\lambda 2$ ($e_2$) [$e_3=1.2\times(e1,e2)$], it is possible to form a spectral image in which microstructures of blood vessels are highlighted. In increasing the gains of the $\lambda 1$, $\lambda 2$ and $\lambda 3$ signals, a specified color is highlighted greatly and noise is also increased accordingly. Therefore, images to be compared in the noise removal circuit 27 are increased from three to four frames, five or six frames, depending on the degree of the increased gain, to reduce the noise.

In the embodiment, the amplifier circuit 46 is arranged inside the spectral image forming circuit 28. Where all the $\lambda 1$, $\lambda 2$ and $\lambda 3$ signals are amplified at the same rate, an automatic gain control circuit of the CDS/AGC circuit 17 arranged inside the scope 10 may be used in place of the amplifier circuit 46. In other words, if the gain of the automatic gain control circuit is increased in forming a spectral image, the spectral image with a favorable brightness can be obtained.

Further, in the embodiment, the noise removal circuit 27 is arranged in the stage prior to the spectral image-forming circuit 28. The noise removal circuit 27 may be arranged inside the spectral image-forming circuit 28, for example, at the stage subsequent to the amplifier circuit 46. In addition, regarding the reverse gamma processing, the DSP 25 shown in FIG. 2 may be changed and controlled so that no gamma processing is conducted in forming a spectral image and the reverse gamma processing circuit 42 is not provided inside the spectral image-forming circuit 28.

In the endoscope apparatus of the present invention, reduction in brightness due to the constitution with narrow-band wavelength ranges can be solved, thereby making it possible to form and display a spectral image excellent in brightness level. It is also possible to suppress increases in noise components due to amplification and keep spectral images in good quality. Further, specified microstructures such as blood vessels and specifically-colored tissues can be extracted to provide valuable information on an object to be observed, which is helpful in making a diagnosis.

The entire disclosure of each and every foreign patent application from which the benefit of foreign priority has been claimed in the present application is incorporated herein by reference, as if fully set forth.

What is claimed is:

1. An endoscope apparatus comprising:
    an endoscope comprising an imaging device that forms a color image signal of a body to be observed;
    a storage portion that stores matrix data for forming a spectral image based on the color image signal;
    a spectral image-forming circuit that conducts matrix calculation based on the color image signal by using the matrix data of the storage portion and forms at least one spectral image signal each of which corresponds to an arbitrarily selected wavelength range; and
    an amplifier circuit that amplifies said at least one spectral image signal formed by the spectral image-forming circuit, wherein
    the color image signal from the imaging device is selectably:
    (i) passed through the spectral image-forming circuit to form said at least one spectral image signal; or
    (ii) not passed through the spectral image-forming circuit to form an ordinary color image signal for an ordinary display, and
    wherein the endoscope apparatus further comprises a noise removal circuit for removing noise of the ordinary color image signal or said at least one spectral image signal, and
    the noise removal circuit conducts noise processing for said at least one spectral image signal at a first noise removal rate and conducts noise processing for the ordinary color image signal at a second noise removal rate, the first noise removal rate being higher than the second noise removal rate.

2. The endoscope apparatus according to claim 1,
    wherein said at least one spectral image signal comprises a plurality of spectral image signals corresponding to a plurality of wavelength ranges, and
    the amplifier circuit amplifies said plurality of image signals at individual different gains.

3. The endoscope apparatus according to claim 1,
    wherein the noise removal circuit increases the first noise removal rate as a gain of the amplifier circuit increases, and the noise removal circuit decreases the first noise removal rate as a gain of the amplifier circuit decreases.

4. The endoscope apparatus according to claim 1,
    wherein the color image signal input to the spectral image-forming circuit is:
    (i) obtained by releasing gamma correction in a signal processing circuit at a front stage of the spectral image-forming circuit; or
    (ii) obtained via a reverse gamma-correction processing circuit, and
    wherein the spectral image-forming circuit forms said at least one spectral image signal based on the color image signal to which no gamma correction is given, and then gamma correction is provided to said at least one spectral image signal.

* * * * *